US010181014B2

(12) United States Patent
Iantorno et al.

(10) Patent No.: US 10,181,014 B2
(45) Date of Patent: Jan. 15, 2019

(54) APPARATUS AND METHODS FOR STORING AND DISPENSING MEDICATIONS

(71) Applicant: MediFriend, Inc., Solana Beach, CA (US)

(72) Inventors: Pat Iantorno, Austin, TX (US); Kent Vander Velden, Johnston, IA (US); Stefan Kanetis, Del Mar, CA (US); Jeff D'Ambrogia, Petaluma, CA (US); Joshua Foss, Round Rock, TX (US); Russell Aldridge, Round Rock, TX (US); Isaac Jones, Round Rock, TX (US); Austin Christenson, Round Rock, TX (US); Joshua Bennett, Round Rock, TX (US); Marc Christenson, Round Rock, TX (US); Max Iantorno, Solana Beach, CA (US); Samuel Neuendorf, Del Mar, CA (US); Tomas Savigliano, San Francisco, CA (US)

(*) Notice: Subject to any disclaimer, the term of this patent is extended or adjusted under 35 U.S.C. 154(b) by 0 days.

(21) Appl. No.: 15/058,532

(22) Filed: Mar. 2, 2016

(65) Prior Publication Data
US 2016/0259914 A1    Sep. 8, 2016

Related U.S. Application Data

(60) Provisional application No. 62/127,244, filed on Mar. 2, 2015.

(51) Int. Cl.
*G06F 19/00* (2018.01)
*G07F 17/00* (2006.01)

(52) U.S. Cl.
CPC .......... *G06F 19/3462* (2013.01); *G06F 19/00* (2013.01); *G07F 17/0092* (2013.01)

(58) Field of Classification Search
CPC ...................................... G07F 11/165
USPC ........................... 198/468.9, 468.2
See application file for complete search history.

(56) References Cited

U.S. PATENT DOCUMENTS

| | | | |
|---|---|---|---|
| 3,624,792 A | 11/1971 | Ernest | |
| 4,411,351 A | 10/1983 | Lowder et al. | |
| 4,814,592 A * | 3/1989 | Bradt | G06Q 20/342 235/375 |
| 5,335,822 A * | 8/1994 | Kasper | B65H 3/24 221/198 |
| 5,468,110 A | 11/1995 | McDonald et al. | |

(Continued)

FOREIGN PATENT DOCUMENTS

| JP | 2011194030 | 10/2011 |
|---|---|---|
| WO | 2014197855 A1 | 12/2014 |

*Primary Examiner* — Timothy R Waggoner
*Assistant Examiner* — Stephen L Akridge
(74) *Attorney, Agent, or Firm* — Vander Velden Law Firm, LLC; Melinda S. Vander Velden

(57) ABSTRACT

An apparatus for automated storage and dispensing of medications. Medications are stored in an inventory storage container attached to a frame of the apparatus. Medications are delivered to the apparatus via a locked delivery container. A carrier mechanism retrieves medications from the inventory storage container and delivery container and moves medications to various subsystems of the apparatus. Information related to medications is communicated to a remote pharmacist prior to dispensing the medication. Multiple installations of the apparatus are centrally coordinated.

6 Claims, 16 Drawing Sheets

(56) References Cited

U.S. PATENT DOCUMENTS

| | | | |
|---|---|---|---|
| 5,561,604 A | 10/1996 | Buckley et al. | |
| 5,593,267 A | 1/1997 | McDonald et al. | |
| 6,152,364 A | 11/2000 | Schoonen et al. | |
| 6,230,927 B1 | 5/2001 | Schoonen et al. | |
| 6,352,200 B1 | 3/2002 | Schoonen et al. | |
| 6,529,801 B1 | 3/2003 | Rosenblum | |
| 6,892,941 B2 | 5/2005 | Rosenblum | |
| 6,929,149 B2 | 8/2005 | Selfridge et al. | |
| 7,063,232 B2 | 6/2006 | Chirnomas | |
| 7,251,546 B2 | 7/2007 | Chirnomas | |
| 7,334,701 B2 | 2/2008 | Chirnomas et al. | |
| 7,407,064 B2 | 8/2008 | Chirnomas | |
| 7,444,203 B2 | 10/2008 | Rosenblum | |
| 7,469,820 B2 | 12/2008 | Rosenblum | |
| 7,471,993 B2 | 12/2008 | Rosenblum | |
| 7,774,097 B2 | 8/2010 | Rosenblum | |
| 7,896,243 B2 | 3/2011 | Herskovitz | |
| 8,033,424 B2 | 10/2011 | Rosenblum | |
| 8,095,236 B2 | 1/2012 | Rudy et al. | |
| 8,191,719 B2 | 6/2012 | Ooyen et al. | |
| 8,267,310 B2 | 9/2012 | Waugh et al. | |
| 8,465,243 B2 | 6/2013 | Ooyen et al. | |
| 8,527,090 B2 | 9/2013 | Monto et al. | |
| 8,577,145 B2 | 11/2013 | Panetta | |
| 8,647,573 B2 | 2/2014 | Regan et al. | |
| 8,695,814 B2 | 4/2014 | Ooyen et al. | |
| 8,712,586 B2 | 4/2014 | Allinson | |
| 8,738,177 B2 | 5/2014 | Ooyen et al. | |
| 8,744,619 B2 | 6/2014 | Rosenblum | |
| 8,789,748 B2 | 7/2014 | Waugh et al. | |
| 8,849,449 B2 | 9/2014 | Waugh et al. | |
| 8,862,266 B2 | 10/2014 | Ooyen et al. | |
| 9,036,894 B2 | 5/2015 | Panetta | |
| 9,495,465 B2 * | 11/2016 | Bowers | G06F 17/3087 |
| 2003/0136794 A1 | 7/2003 | Chirnomas | |
| 2003/0234259 A1 | 12/2003 | Selfridge et al. | |
| 2004/0004085 A1 * | 1/2004 | Williams | G07F 11/44 |
| | | | 221/278 |
| 2004/0026441 A1 | 2/2004 | Chirnomas | |
| 2004/0164146 A1 * | 8/2004 | Rosenblum | G06F 19/00 |
| | | | 235/381 |
| 2004/0215369 A1 | 10/2004 | Rosenblum | |
| 2005/0211720 A1 | 9/2005 | Chirnomas | |
| 2005/0263536 A1 | 12/2005 | Selfridge et al. | |
| 2006/0074524 A1 | 4/2006 | Chirnomas | |
| 2006/0124656 A1 * | 6/2006 | Popovich, Jr. | G07F 9/026 |
| | | | 221/9 |
| 2006/0149587 A1 | 7/2006 | Hill et al. | |
| 2007/0043469 A1 * | 2/2007 | Draper | G06F 19/3462 |
| | | | 700/231 |
| 2007/0162184 A1 | 7/2007 | Pinney et al. | |
| 2007/0250346 A1 | 10/2007 | Luciano et al. | |
| 2007/0293982 A1 | 12/2007 | Rosenblum | |
| 2008/0135574 A1 * | 6/2008 | Hieb | G07F 11/10 |
| | | | 221/123 |
| 2008/0164279 A1 | 7/2008 | Chirnomas et al. | |
| 2008/0272142 A1 | 11/2008 | Chirnomas | |
| 2009/0048712 A1 | 2/2009 | Rosenblum | |
| 2009/0076650 A1 | 3/2009 | Faes | |
| 2009/0144208 A1 * | 6/2009 | Blust | G06Q 10/08 |
| | | | 705/500 |
| 2010/0198401 A1 | 8/2010 | Waugh et al. | |
| 2010/0232640 A1 | 9/2010 | Friend et al. | |
| 2010/0268380 A1 * | 10/2010 | Waugh | G07F 11/44 |
| | | | 700/239 |
| 2010/0324728 A1 | 12/2010 | Rosenblum | |
| 2011/0264259 A1 | 10/2011 | Boyer et al. | |
| 2012/0004770 A1 | 1/2012 | Ooyen et al. | |
| 2012/0012606 A1 | 1/2012 | Longley et al. | |
| 2012/0089249 A1 | 4/2012 | Rosenblum | |
| 2012/0232693 A1 | 9/2012 | Allinson | |
| 2013/0251479 A1 | 9/2013 | Waugh et al. | |
| 2014/0154044 A1 | 6/2014 | Ooyen et al. | |
| 2014/0361076 A1 | 12/2014 | Iantorno et al. | |
| 2015/0019008 A1 | 1/2015 | Ooyen et al. | |
| 2015/0025679 A1 | 1/2015 | Rosenblum | |
| 2015/0134106 A1 | 5/2015 | Boyer et al. | |
| 2015/0203297 A1 * | 7/2015 | Manning | F25D 13/06 |
| | | | 700/218 |
| 2016/0188840 A1 * | 6/2016 | Eramian | G06F 19/3462 |
| | | | 700/237 |
| 2017/0132867 A1 * | 5/2017 | Berg | G07F 11/005 |

\* cited by examiner

APPARATUS AND METHODS FOR STORING AND DISPENSING MEDICATIONS

CROSS-REFERENCE TO RELATED APPLICATIONS

This application claims priority to U.S. Provisional Patent Application No. 62/127,244, filed on Mar. 2, 2015, the entirety of which is hereby incorporated herein by reference.

FIELD OF THE INVENTION

This invention relates generally to medication dispensers and methods for storing and dispensing medications. In particular, this invention provides a centrally coordinated automated medication dispenser configured to be monitored remotely by a pharmacist who oversees one or more automated medication dispensers, thereby increasing the efficiency of the medication dispensing process. Further efficiencies are achieved by improved logistics, trend observations, and geolocating via a phone application.

BACKGROUND

Traditionally, dispensing of medications has been performed exclusively in a pharmacy setting in which one or more pharmacists must be physically present. Legal requirements in some jurisdictions mandate a certain number of pharmacies per geographical area, resulting in a large number of pharmacies, each of which must be staffed by at least one pharmacist. Because each pharmacist can only serve one pharmacy, a large number of highly trained individuals is needed to staff the many traditional pharmacies in existence, resulting in great expense.

In addition to the expense of supporting traditional pharmacies, a relatively large number of individuals may have unmonitored access to medications stored in traditional pharmacy inventories. This uncontrolled access results in a large number of medications that go missing without the ability to determine precisely who took the medication.

Attempts have been made to remedy the inefficiencies presented by traditional pharmacies with kiosks; however, the medication dispensing kiosks available still rely heavily on pharmacist interaction. In some instances, a pharmacist must restock medications. In other instances, the kiosk functions only to place the pharmacist remotely from the kiosk, and a pharmacist must still instigate and complete the medication dispensing process. The available kiosks also do not address the issue of medication security as medication packages are directly handled by a technician and placed by hand into the kiosk. For at least these reasons, an apparatus that automatically restocks and dispenses medications with minimal interaction by a pharmacist would be advantageous.

BRIEF SUMMARY

In accordance with one embodiment of the invention, an apparatus for storing and dispensing medications contained in a bottle or other packaging is provided. The apparatus comprises an inventory storage container that is configured to store a number of medication packages within the apparatus. Medications to be stored in the inventory storage container may be provided in a locked delivery container, and the apparatus is capable of automatically unloading the delivery container to place medications held by the delivery container into the inventory storage container. Medications are removed from the inventory storage container or delivery container by a carrier that is configured to move the medications between various sub-assemblies of the apparatus. A printer assembly is provided to print labels to be adhered on the medication packaging. A computer disposed in the apparatus controls the function of the various other components of the apparatus, communicates with a centralized database that stores patient and medication information and manages inventory. An input device disposed on the apparatus allows technicians, patients, and other users to interact with the apparatus.

Through the use of locked delivery container, the apparatus may be securely restocked by a technician while complying with legal requirements of a jurisdiction. In one embodiment, restocking the apparatus comprises authenticating a technician to access the apparatus. Once the technician is authorized, the apparatus unlocks an access panel, allowing the technician to place the locked delivery container in the apparatus. The apparatus is then locked, and the apparatus automatically unloads the delivery container, identifies the medications that have been placed within it, and places the newly added medications in the inventory storage container.

Medications may be dispensed to patients with minimal intervention by a pharmacist. A patient refills a prescription by first providing identifying information to the apparatus through an input device such as a touchscreen. The apparatus verifies that the patient has a valid prescription for the requested medication through communication with the centralized database. The apparatus also determines if the apparatus contains the medication the patient has requested. The medication is pushed from its location in the inventory storage container, labelled, scanned by a barcode reader, and an image is captured. The patient's prescription and images of the medication before and after labelling are communicated to a pharmacist, who inspects the information communicated from the apparatus to the pharmacist and may approve or reject dispensing the medication to the patient based on the inspection. This embodiment of a dispensing process is advantageous because it minimizes the pharmacist's interaction, yet satisfies the legal requirements of many jurisdictions.

Lock boxes located externally to the apparatus may be used to store dispensed medications, extending the capacity of the inventory storage container. Access to the lock boxes is controlled by the apparatus, and a technician may move the medications into the lock boxes.

Software running on a phone or similar device may be used to find the nearest apparatus containing all medications required by the user.

Required inventory may be predicted based on trends observed in dispensing history.

While the embodiments described refer to medications, other items may be similarly stored and dispensed from the described apparatus.

BRIEF DESCRIPTION OF THE DRAWINGS

Figure 1:
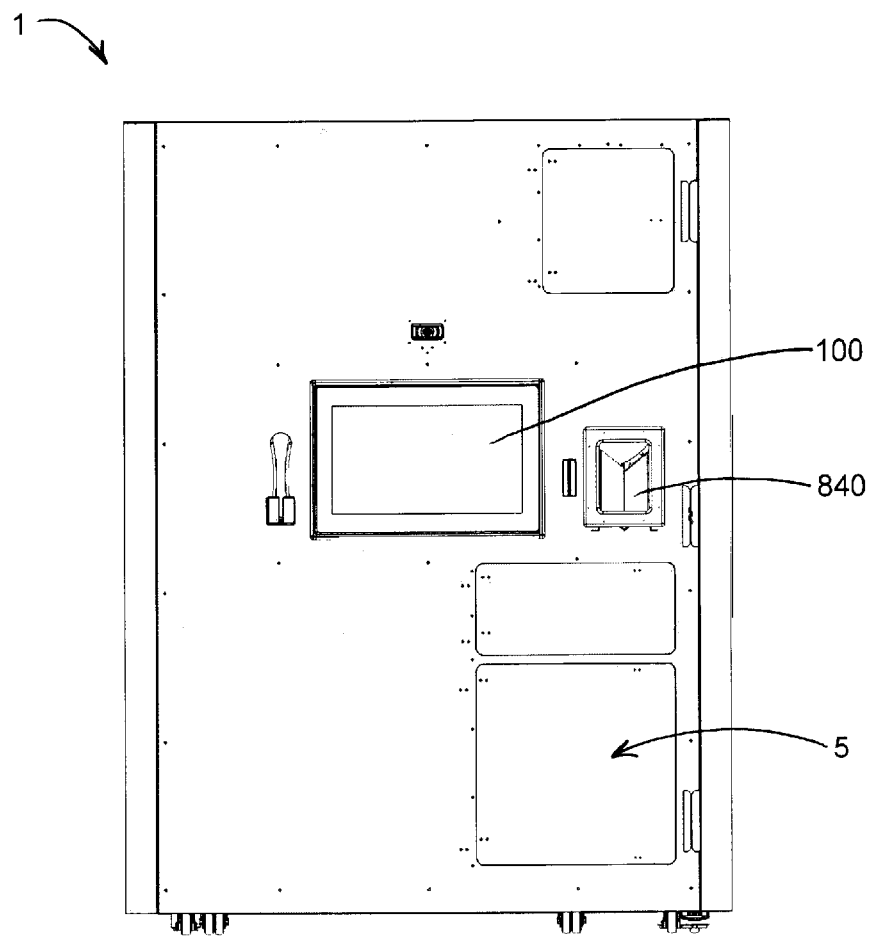

Having thus described the invention in general terms, reference will now be made to the accompanying drawings, which are not necessarily drawn to scale, and wherein:

FIG. 1 illustrates a front external view of an apparatus for storing and dispensing items such as medications in accordance with an embodiment of the invention.

Figure 2:
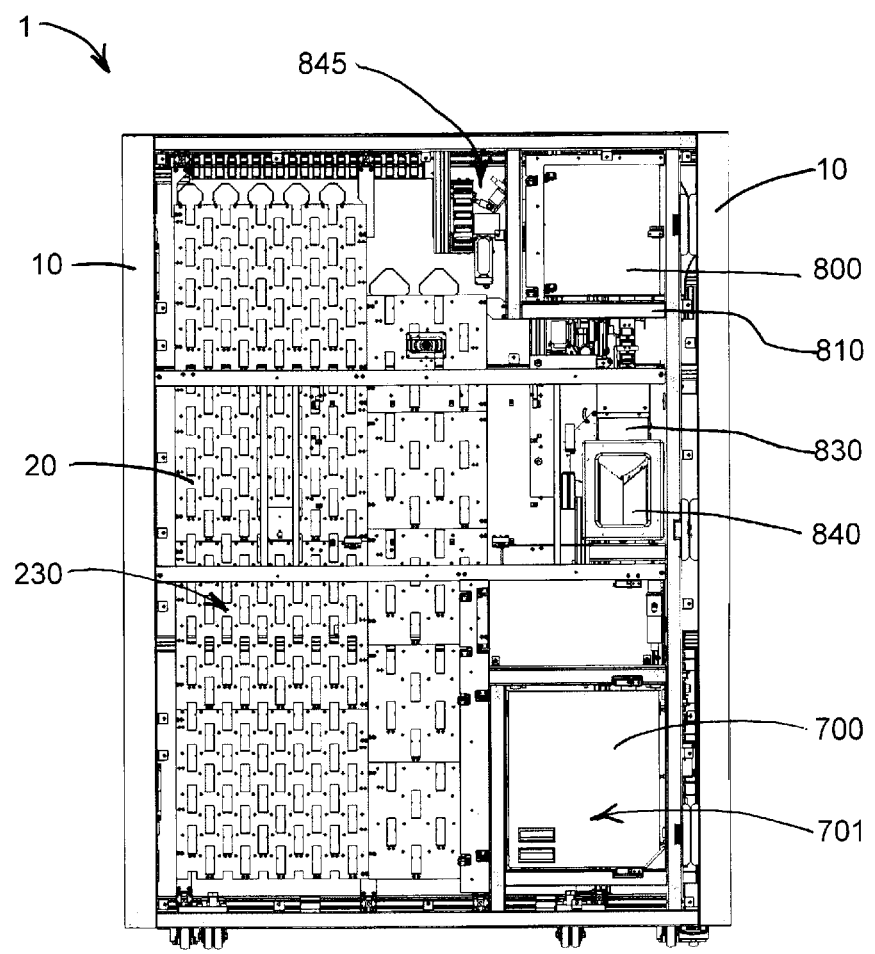

FIG. 2 illustrates a front view of the internal structure of an apparatus for storing and dispensing items such as medications in accordance with an embodiment of the invention.

Figure 3:
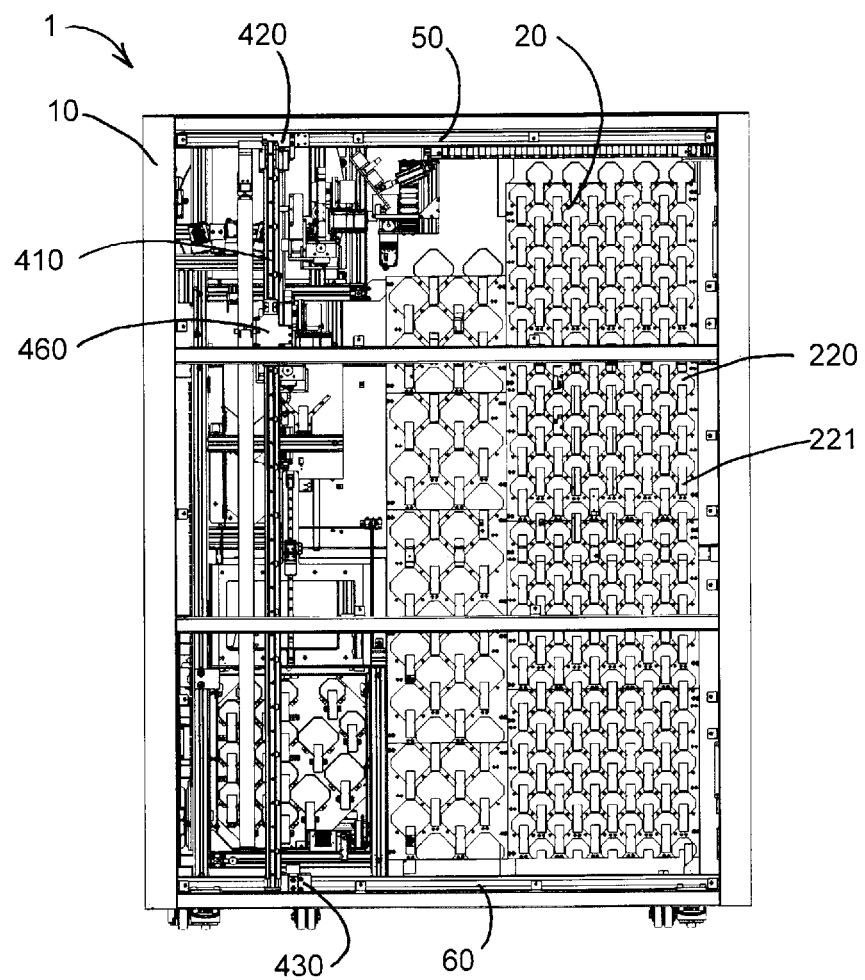

FIG. 3 illustrates a rear view of the internal structure of an apparatus for storing and dispensing items such as medications in accordance with an embodiment of the invention.

Figure 4:
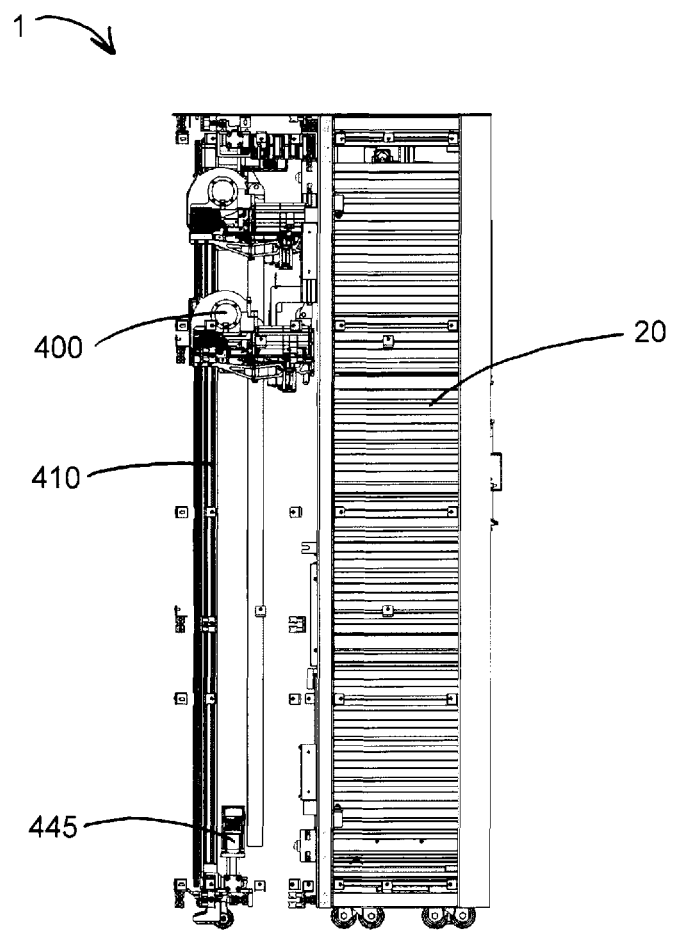

FIG. 4 illustrates a side view of the internal structure of an apparatus for storing and dispensing items such as medications in accordance with an embodiment of the invention.

Figure 5:
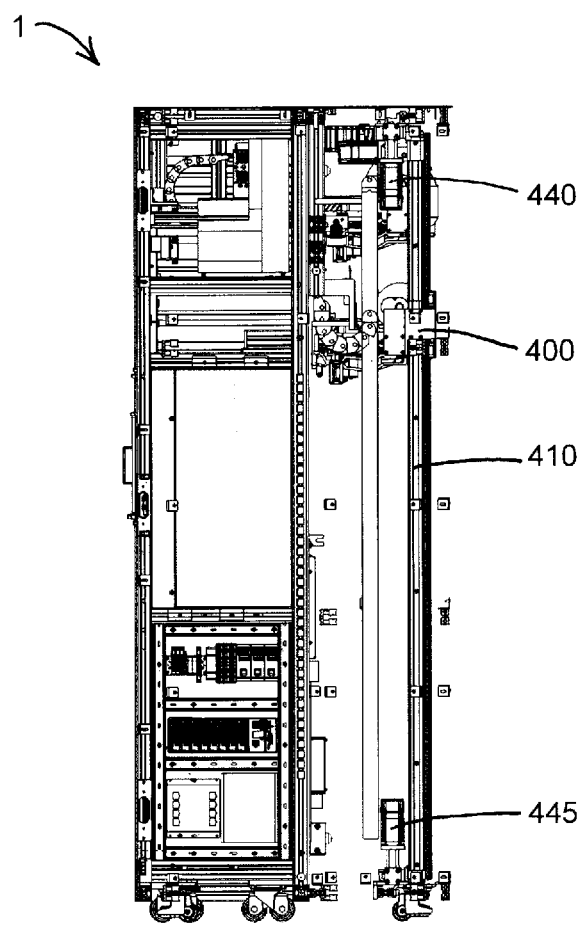

FIG. 5 illustrates a side view of the internal structure of an apparatus for storing and dispensing items such as medications in accordance with an embodiment of the invention.

Figure 6:
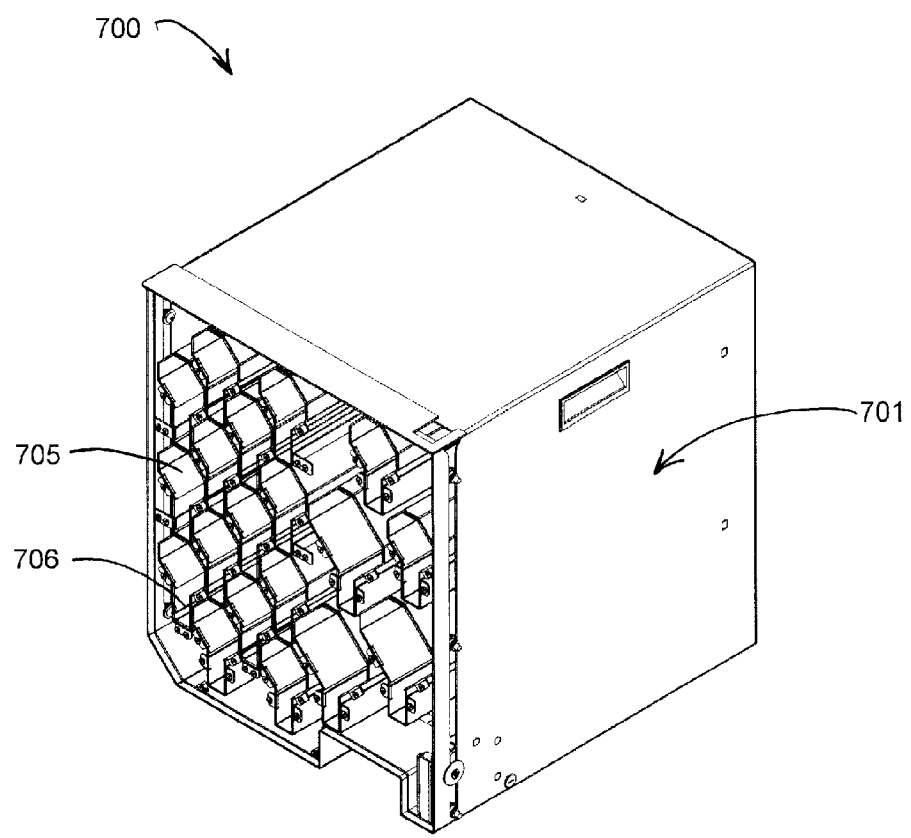

FIG. 6 illustrates a delivery container in accordance with an embodiment of the invention.

Figure 7:
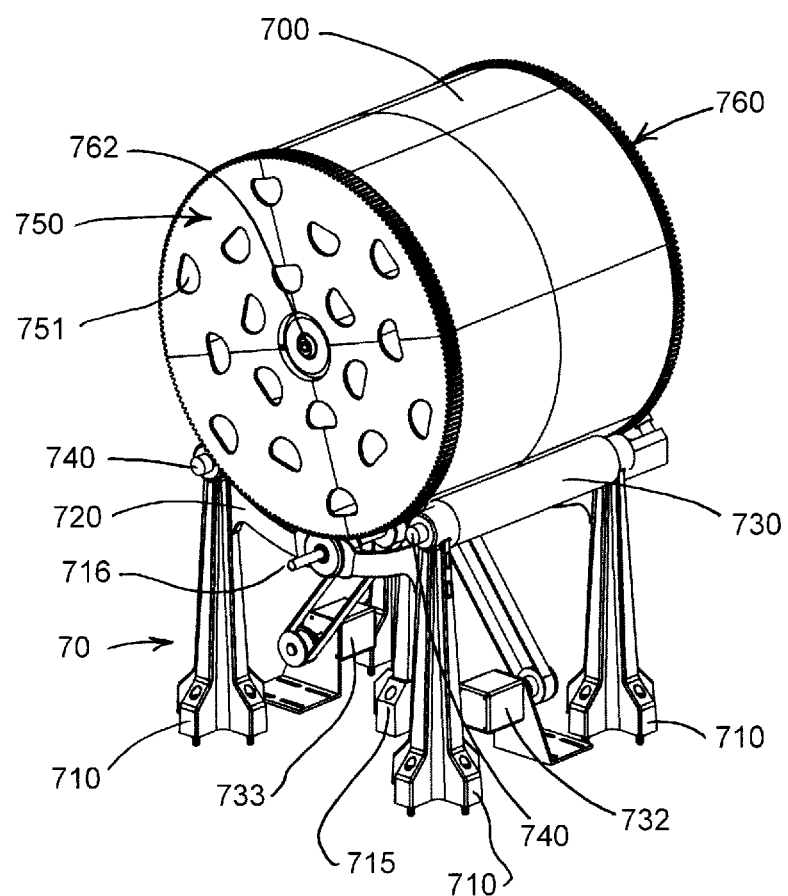

FIG. 7 illustrates an alternative embodiment of a delivery container and a delivery container support assembly in accordance with an embodiment of the invention.

Figure 8:
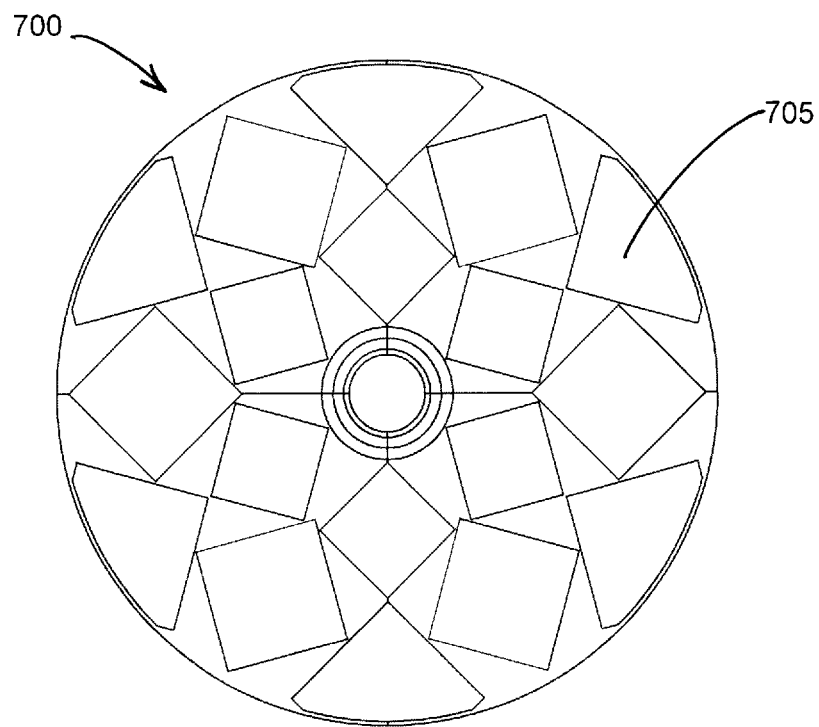

FIG. 8 illustrates the internal structure of an alternative embodiment of a delivery container in accordance with an embodiment of the invention.

Figure 9:
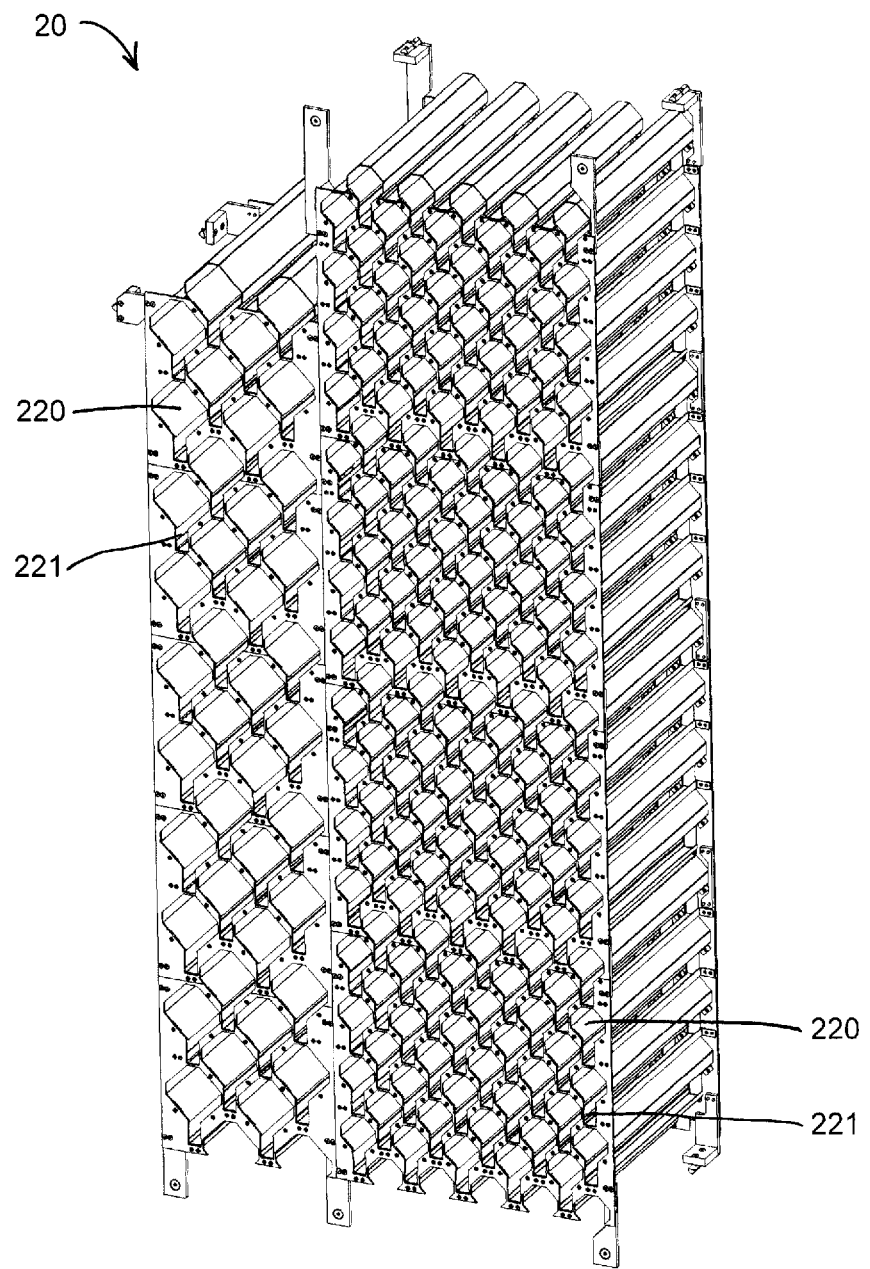

FIG. 9 illustrates an inventory storage container for storing items such as medications in accordance with an embodiment of the invention.

Figure 10:
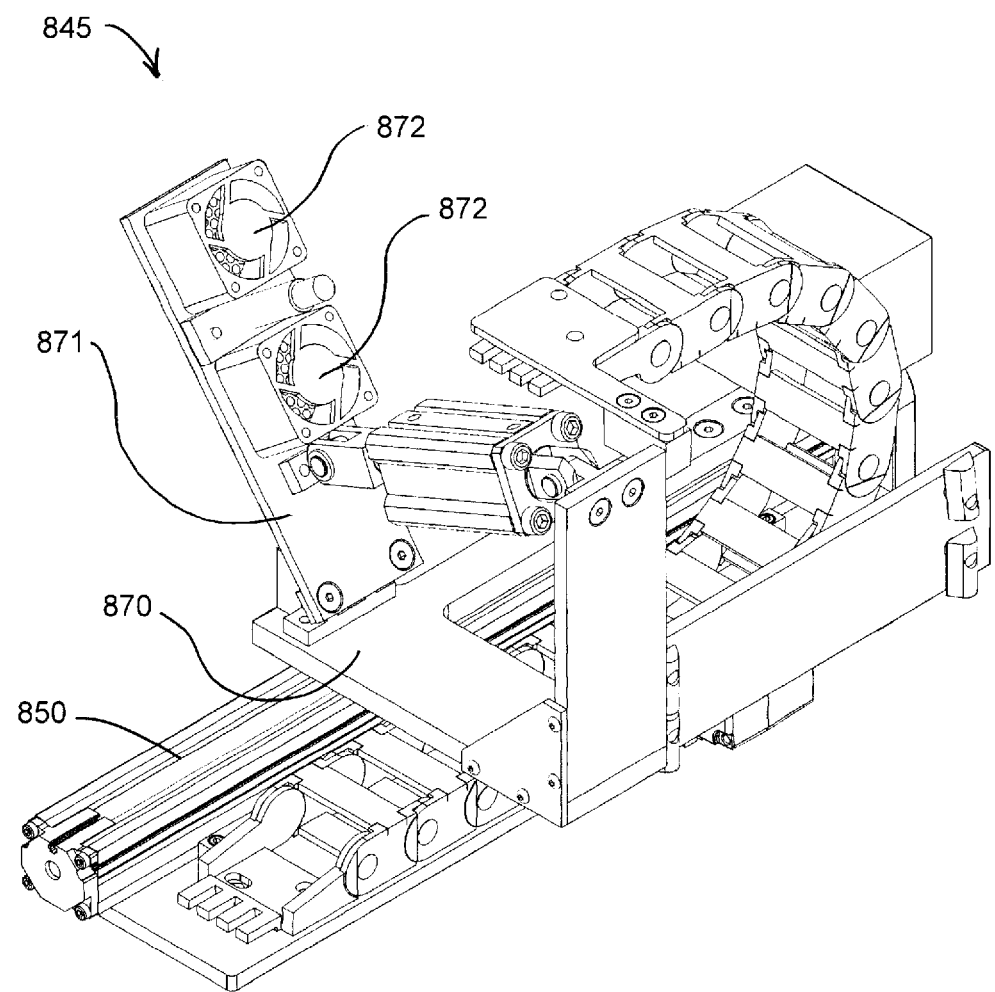

FIG. 10 illustrates a label handling assembly in accordance with an embodiment of the invention.

Figure 11:
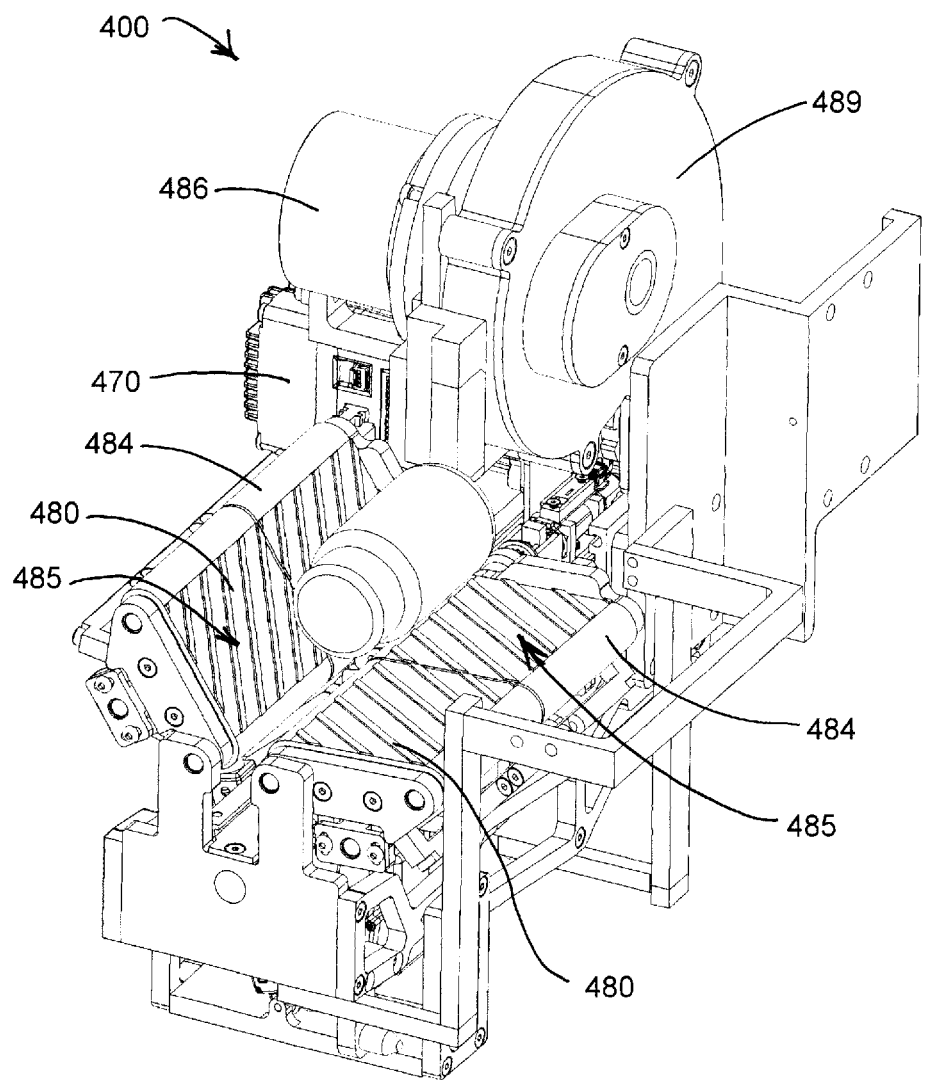

FIG. 11 illustrates a carrier in accordance with an embodiment of the invention.

Figure 12:
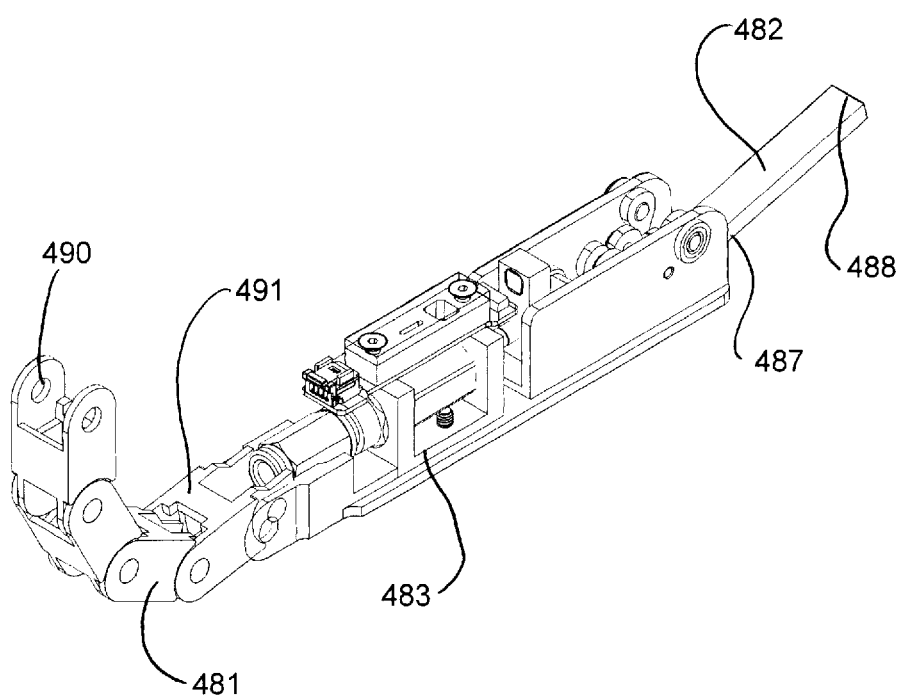

FIG. 12 illustrates an extendable member and flipper in accordance with an embodiment of the invention.

Figure 13:
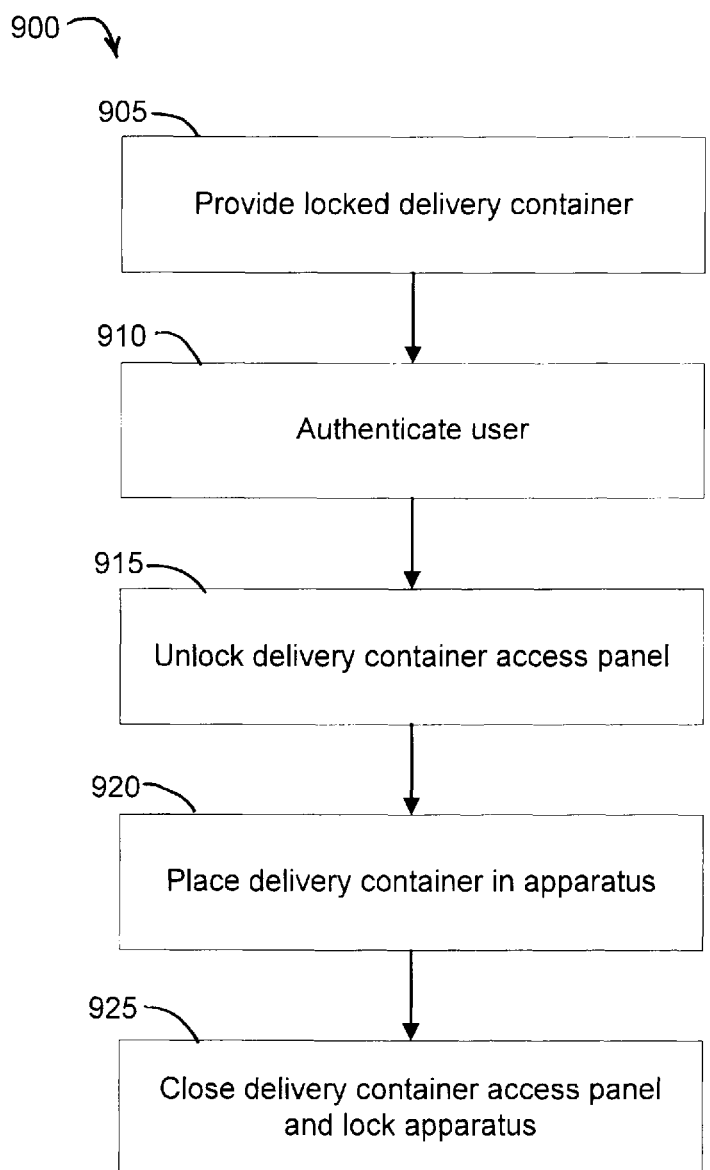

FIG. 13 illustrates a method for replacing a delivery container in accordance with an embodiment of the invention.

Figure 14:
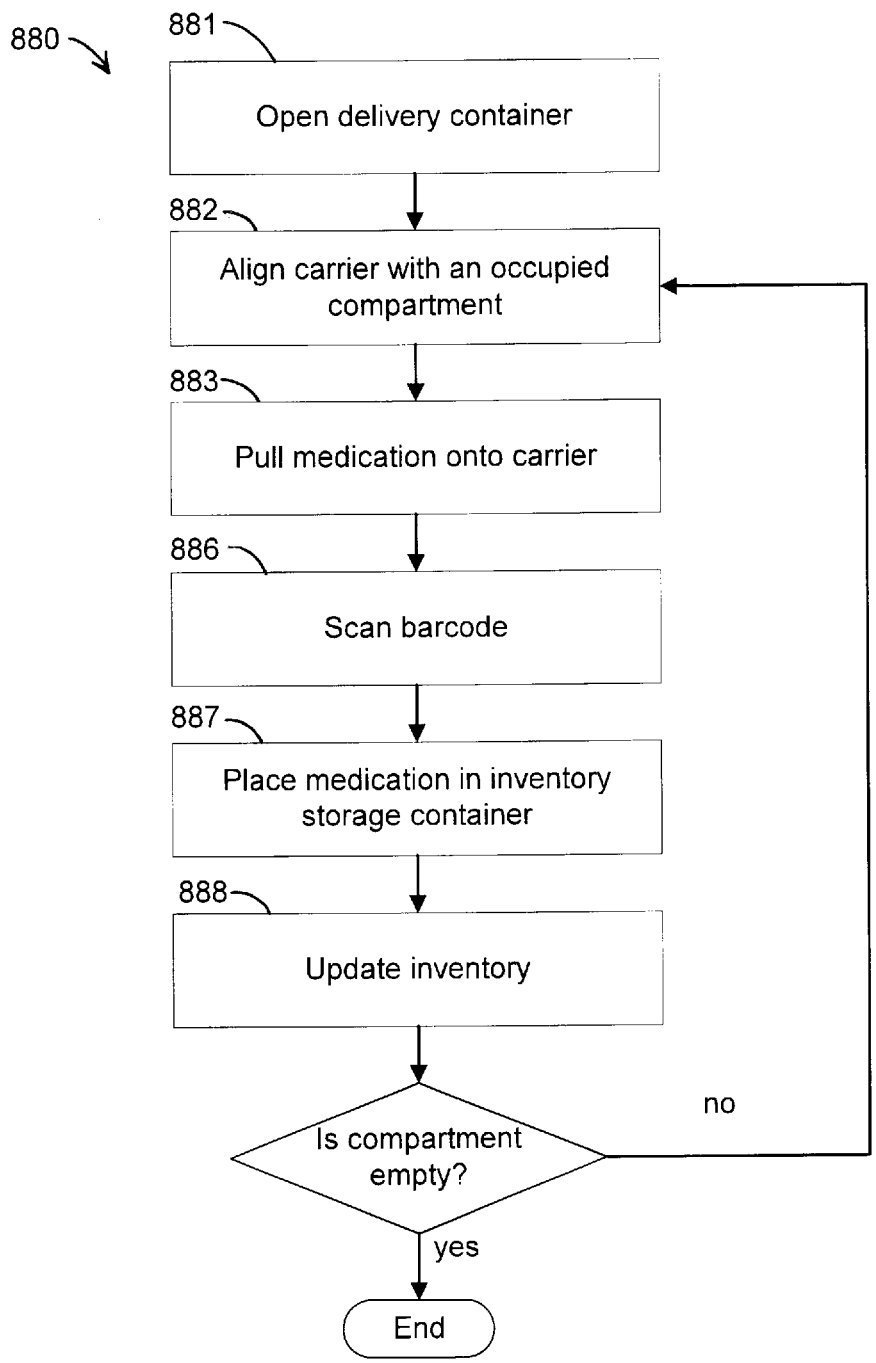

FIG. 14 illustrates a method for stocking an inventory storage container in accordance with an embodiment of the invention.

Figure 15:
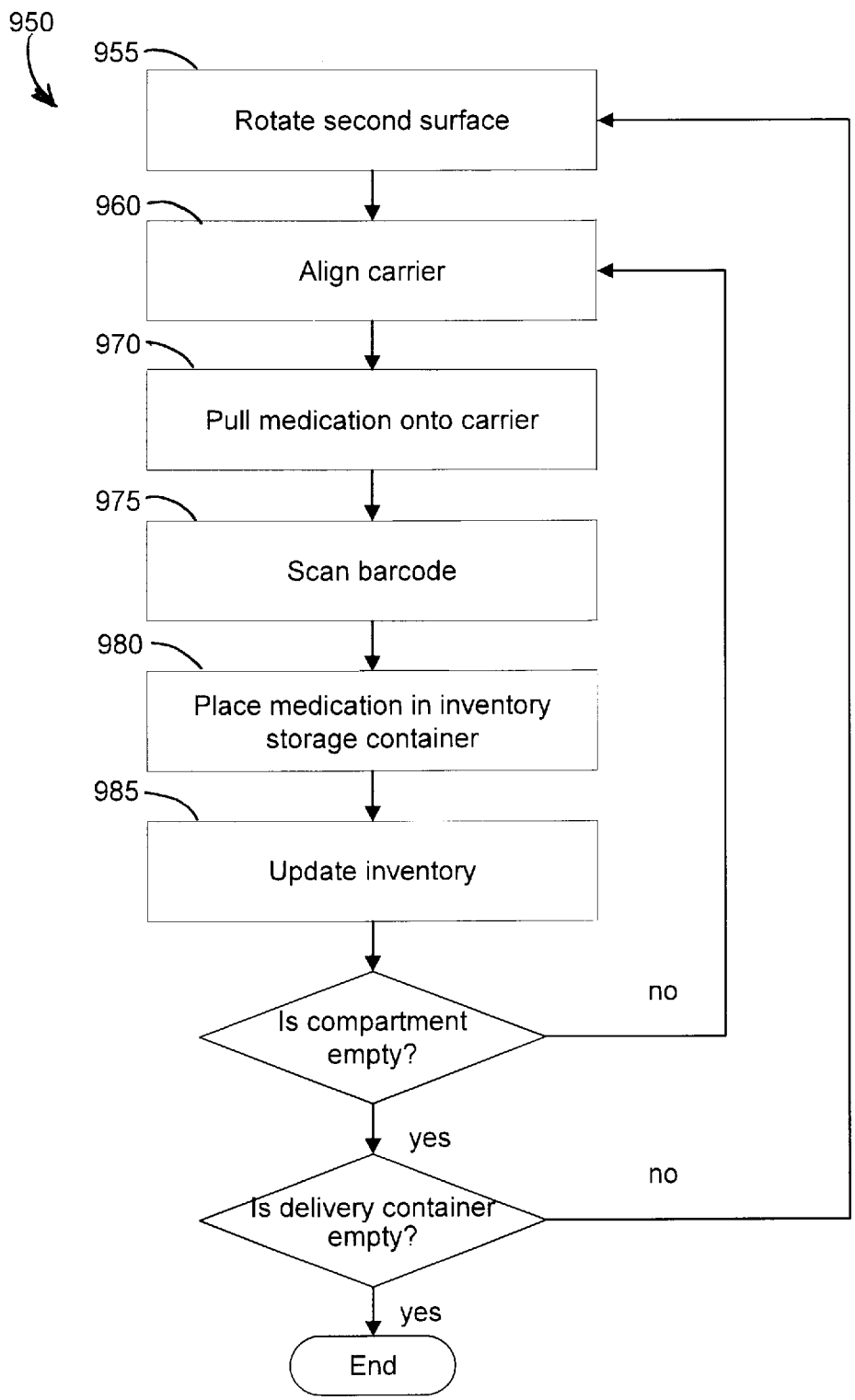

FIG. 15 illustrates an alternative method for stocking an inventory storage container in accordance with an embodiment of the invention.

Figure 16:
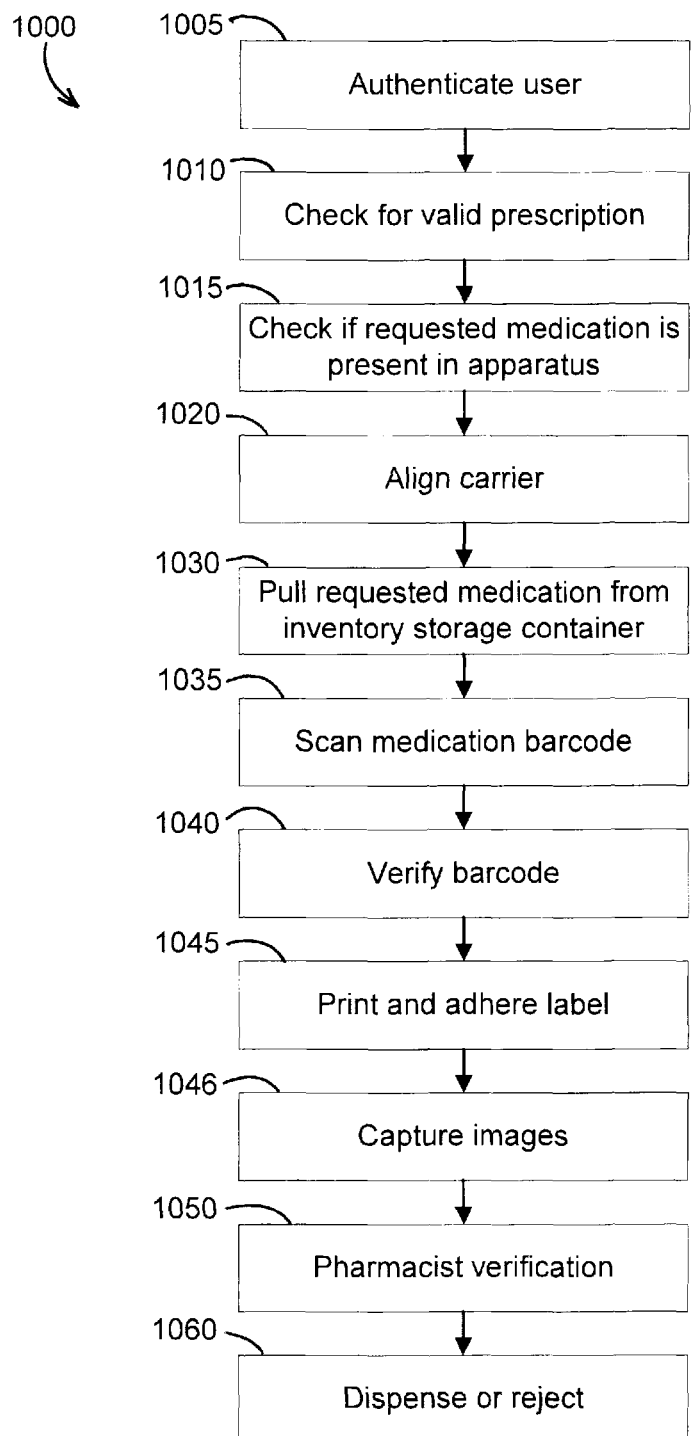

FIG. 16 illustrates a method for dispensing a medication in accordance with an embodiment of the invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. Some components of the apparatus are not shown in one or more of the figures for clarity and to facilitate explanation of embodiments of the present invention.

In accordance with one embodiment, FIG. 1, FIG. 2, FIG. 3, FIG. 4, and FIG. 5 illustrate an apparatus 1 for storing and dispensing medications. In one embodiment, apparatus 1 comprises a frame 10. An inventory storage container 20 for storing medications, stationary tracks 50 and 60, a printer assembly, a computer, and an input device 100 are attached to frame 10.

An enclosure may attach to the frame 10 to completely surround the apparatus 1 and prevent access to the control electronics and other internal components of the apparatus 1 and items stored in the apparatus 1. In one embodiment, the enclosure comprises a plastic covering. In other embodiments, the enclosure may comprise a covering made from metal, wood, or another material capable of enclosing the internal components of the apparatus 1.

Frame

Frame 10 defines a generally box-shaped structure capable of providing stable mounting points for other components of the apparatus 1. Frame 10 may comprise rails defining the corners of the box-shaped structure. Frame 10 may further comprise additional rails or cross bracing to provide stability or mounting points for components of the apparatus 1. Frame 10 may be constructed from metal, wood, plastic, or other rigid material capable of attaching to and supporting other structures and sub-systems of the apparatus 1. Wires connecting various parts of the apparatus may be routed through the frame 10 such that wiring is not exposed.

Carrier Assembly

In one embodiment, a carrier 400 is configured to retrieve items and move items between sub-systems of the apparatus 1. The carrier 400 can be moved horizontally and vertically, allowing the carrier 400 to access any compartment 220 of the inventory storage container 20, any compartment 705 of the delivery container 700, or any other sub-system of the apparatus 1.

A stationary track 50 extends from a first rail of the frame 10 to the parallel rail of the frame 10 on the same side of the apparatus 1. Likewise, stationary track 60 extends from the same first rail of the frame 10 to the same parallel rail of the frame 10 on the same side of the apparatus 1. Stationary track 50 is situated near the top of the frame 10, stationary track 60 is situated near the bottom of the frame 10, and stationary tracks 50 and 60 are parallel to each other. Stationary tracks 50 and 60 are fixedly attached to the frame 10.

A moving carrier track 410 extends from stationary track 50 to stationary track 60. An upper end of the moving carrier track 410 may be connected to stationary track 50 by an upper carrier track carriage 420 that engages a channel in stationary track 50. Similarly, a lower end of the moving carrier track 410 may be connected to stationary track 60 by a lower carrier track carriage 430 that engages a channel in stationary track 60. A belt situated within the channel of stationary track 50 engages both the upper carrier track carriage 420 and the shaft of an upper carrier track motor 440. Another belt situated within the channel of stationary track 60 engages both the lower carrier track carriage 430 and the shaft of a lower carrier track motor 445. By rotating the shaft of the upper carrier track motor 440 and the lower carrier track motor 445, the moving carrier track 410 is moved horizontally. In one embodiment, a connecting rod attached to the shaft of either upper carrier track motor 440 or lower carrier track motor 445 extends between stationary tracks 50 and 60 and engages each belt situated within the channels of each of stationary tracks 50 and 60, allowing one motor to drive both of the belts responsible for the movement of the moving carrier track 410. By using one motor and a connecting rod in this manner, the speeds of and distances traveled by the upper carrier track carriage 420 and the lower carrier track carriage 430 are the same. Limit switches may be located at each end of stationary tracks 50 and 60 to indicate when the carrier track carriages 420 and 430 have reached the ends of their travel ranges.

A carrier carriage 460 engages a channel in the moving carrier track 410. A belt situated within the channel of the moving carrier track 410 engages the carrier carriage 460 and the shaft of a carrier carriage motor 470. By rotating the shaft of the carrier carriage motor 470, the carrier carriage 460 is moved vertically along the moving carrier track 410. Limit switches may be located at each end of the moving carrier track 410 to indicate when the carrier carriage 460 has reached the ends of its travel range.

The carrier 400 is mounted to the carrier carriage 460. As shown in FIG. 11, the carrier 400 comprises one or more container engaging surfaces 480 capable of engaging and holding a container. Multiple container engaging surfaces 480 may be positioned relative to each other in order to form an angle that prevents containers being held by the container engaging surfaces 480 from rolling off the carrier 400. Each container engaging surface 480 comprises one or more rollers 484, each roller 484 being generally parallel to other rollers 484 of that container engaging surface 480. One or more carrier roller belts 485 engage and surround the rollers 484 of a container engaging surface 480. A container being held on carrier 400 may be rotated by rotating the one or more rollers 484 of the one or more container engaging surfaces 480. As rollers 484 are rotated, the one or more belts 485 are moved; thus causing the container held on carrier 400 to rotate. Rotation of rollers 484 may be accomplished by a motor, servo, or other device capable of rotating the rollers 484.

As shown in FIG. 12, the carrier 400 further comprises an extendable member 481 configured to pass beneath container engaging surfaces 480, and to extend into and engage containers stored in an inventory storage container compartment 220 or a delivery container compartment 705. The extendable member 481 comprises a chain, cable, strip, or other material capable of being held rigid when extended and rolled into a coil when not extended. When extended, the extendable member 481 is capable of extending the full depth of the inventory storage container 20 or delivery container 700.

A first end 490 of extendable member 481 is connected to the shaft of an extendable member motor 486. Extension of the extendable member 481 may be accomplished by rotating the shaft of the extendable member motor 486 in a first direction, causing the extendable member 481 to extend. Retraction of the extendable member 481 may be accomplished by rotating the shaft of the extendable member motor 486 in the opposite direction, causing the extendable member 481 to return to a coiled state. A tensioning mechanism may assist with the retraction of the extendable member 481 to prevent the extendable member 481 from binding up as it returns to its coiled state. A sensor may be provided to indicate when the extendable member 481 has been fully extended or retracted. Further, a coil containment compartment 489 disposed on the carrier 400 may surround the extendable member 481 while it is in its retracted and coiled state, causing the extendable member 481 to coil evenly on itself and prevent tangling of the extendable member 481.

Carrier 400 further comprises a flipper 482. Flipper 482 comprises a strip of rigid material having a first flipper end 487 and a second flipper end 488. First flipper end 487 is connected to a second end 491 of extendable member 481 via a flipper actuator 483, and the flipper 482 is capable of being rotated about the first flipper end 487.

To retrieve a container stored in an inventory storage container compartment 220 or a delivery container compartment 705 adjacent to the carrier 400, extendable member motor 486 is rotated in a first direction, causing extendable member 481 to uncoil and extend beneath the container engaging surfaces 480 and into the compartment channel associated with the inventory storage container compartment 220 or delivery container compartment 705. When the first flipper end 487 has reached the end of the container in the inventory storage container compartment 220 or delivery container compartment 705 that is furthest from the carrier 400, flipper 482 is actuated by the flipper actuator 483 to rotate about the first flipper end 487 in a first direction until flipper 482 forms an approximately 90 degree angle to extendable member 481. The extendable member motor 486 can then be rotated in a second direction, causing extendable member 481 to retract, and causing flipper 482 to engage a surface of the container in the inventory storage container compartment 220 or delivery container compartment 705 that is furthest from the carrier 400, pulling the container toward the carrier 400. As the container furthest from the carrier 400 is pulled toward the carrier 400, each additional container situated between the furthest container and the carrier 400 is also pulled toward the carrier 400. This motion of the extendable member 481 continues until a sensor indicates that a container is situated on the container engaging surfaces 480. At this point, flipper 482 is actuated to rotate about the first flipper end 487 in a second direction until flipper 482 is generally parallel to extendable member 481 and can pass beneath the container engaging surfaces 480.

To place a container being held on the carrier 400 into an inventory storage container compartment 220 adjacent to the carrier 400, extendable member motor 486 is rotated as needed to position second flipper end 488 near the end of the container on the carrier 400 that is furthest from the inventory storage container compartment 220. Flipper 482 is then actuated to rotate about the first flipper end 487 in a first direction until flipper 482 forms an approximately 90 degree angle to extendable member 481. The extendable member motor 486 can then be rotated in a first direction, causing extendable member 481 to extend beneath the container engaging surfaces 480, and causing flipper 482 to engage the surface of the container on the carrier 400 that is furthest from the inventory storage container compartment 220, pushing the container toward the inventory storage container compartment 220. As the container on the carrier 400 is pushed into the inventory storage container compartment 220, any containers already situated in the inventory storage container compartment 220 are pushed further into the inventory storage container compartment 220 to accommodate the container being pushed off the carrier 400. This motion of the extendable member 481 continues until a sensor indicates that the flipper 482 has reached the edge of the inventory storage container compartment 220, indicating that the container has been positioned entirely in the inventory storage container compartment 220. At this point, the extendable member motor 486 is rotated in a second direction, causing the extendable member 481 to retract, until flipper 482 can rotate without interfering with containers in the inventory storage container compartment 220. Flipper 482 is then actuated to rotate about the first flipper end 487 in a second direction until flipper 482 is generally parallel to extendable member 481 and can pass beneath the container engaging surfaces 480.

Inventory Storage Container

As shown in FIG. 9, an inventory storage container 20 configured to attach to the frame 10 provides a structure within the apparatus 1 where one or more medications may be stored. Inventory storage container 20 comprises a plurality of compartments 220, wherein each compartment 220 is accessible to the carrier 400. Compartments 220 may be elongated chambers situated within the inventory storage container 20. A compartment channel 221 may extend generally parallel to each compartment 220, and be generally the same length as each compartment 220. Each compartment channel 221 comprises an open space adjacent to its corresponding compartment 220, and is of sufficient height and width to accommodate entry of the extendable member 481. Compartments 220 may vary in size to allow various sizes of medication packaging to be stored while maximizing the number of compartments 220; thus maximizing the number of medications that can be stored in inventory storage container 20. One or more adaptors may be placed in any compartment 220 to allow placement of non-cylindrical or oddly shaped packaging such that it is accessible to the carrier 400.

The side of each compartment 220 that is adjacent to the carrier 400 may be open to allow for the carrier 400 to access medications located in each compartment 220. The opposite end of each compartment 220 may be covered by a cover 230.

Inventory storage container 20 and its individual compartments 220 may be angled such that the end of each compartment 220 that is covered by cover 230 is lower than the opposite and open end. Such angling of inventory storage container 20 and compartments 220 prevents medication packaging from falling out of the inventory storage container 20 if the apparatus 1 experiences vibration, shaking, or other motion.

The inventory storage container 20 may be constructed from metal, wood, cardboard, plastic, or other suitable material.

Delivery Container and Delivery Container Support Assembly

One embodiment of a delivery container 700 is shown in FIG. 6. The delivery container 700 provides a secure structure for introducing new medications into the apparatus 1. Delivery container 700 comprises a lockable delivery container enclosure 701 and a plurality of compartments 705 disposed inside the enclosure 701. Once the delivery container 700 has been placed inside the apparatus 1, and the apparatus 1 has unlocked and opened the enclosure 701, each compartment 705 is accessible to the carrier 400. Compartments 705 may be elongated chambers situated within the delivery container 700. A compartment channel 706 may extend generally parallel to each compartment 705, and be generally the same length as each compartment 705. Each compartment channel 706 comprises an open space adjacent to its corresponding compartment 705, and is of sufficient height and width to accommodate entry of the extendable member 481. Compartments 705 may vary in size to allow various sizes of medication packaging to be stored while maximizing the number of compartments 705; thus maximizing the number of medications that can be stored in the delivery container 700. One or more adaptors may be placed in any compartment 705 to allow placement of non-cylindrical or oddly shaped packaging such that it is accessible to the carrier 400.

An alternative embodiment of the delivery container 700 is shown in FIG. 7 and FIG. 8. This alternative embodiment employs a delivery container support assembly 70. The delivery container support assembly 70 comprises four corner supports 710 wherein each of the four corner supports 710 comprises a first end and a second end. The first end of each corner support 710 attaches to the frame 10 such that each of the corner supports 710 is generally perpendicular to a bottom surface or plane of the apparatus 1, and the placement of the corner supports 710 creates a generally rectangular base for the delivery container 700 to rest upon.

The second ends of two of the two corner supports 710 may be connected together by a brace 720 to form a first side of the delivery container support assembly 70. Similarly, the second ends of the other two corner supports 710 may also be connected together by a brace 720 to form a second side of the delivery container support assembly 70, wherein the second side of the delivery container support assembly 70 is generally parallel to the first side of the delivery container support assembly 70.

The second ends of two of the two corner supports 710 may additionally be connected together by rods 740. The rods 740 connect the first and second sides of the delivery container support assembly 70 together such that the rods 740 are generally parallel to each other and generally perpendicular to the first and second sides of the delivery container support assembly 70. A roller 730 surrounds each of the rods 740 such that each roller 730 is free to rotate about the rod 740 that it surrounds. The rollers 730 provide the surface that the delivery container 700 rests upon.

The delivery container support assembly 70 may further comprise a center support 715 having a first end and a second end. The first end of the center support 715 attaches to the frame 10 such that the center support 715 is generally parallel to the corner supports 710, and such that the attachment point of the first end of the center support 715 is disposed generally in the center of the rectangle formed by the attachment points of the first ends of the corner supports 710 to the frame 10. Connecting rods 716 pass through the second end of the center support 715 and the braces 720 in the first and second sides of the delivery container support assembly 70.

As shown in FIG. 7 and FIG. 8, in this alternative embodiment, the delivery container 700 comprises a cylindrical drum having a first flat surface 750 and a second flat surface 760 wherein the first flat surface 750 is fixedly attached to the body of the delivery container 700 and the second flat surface 760 attaches to the body of the delivery container 700 at the center of the second flat surface 760 such that the second flat surface 760 is capable of rotating independently of the delivery container 700.

The second flat surface 760 comprises a disk having notches disposed around the circumference of the disk wherein the notches are configured to engage a gear disposed on the connecting rod 716 corresponding to the second flat surface 760. A motor 732 drives the gear corresponding to the second flat surface 760, causing the second surface 760 to rotate as the shaft of the motor 732 is rotated. Similarly, the first flat surface 750 comprises a disk having notches disposed around the circumference of the disk wherein the notches are configured to engage a second gear disposed on the connecting rod 716 corresponding to the first flat surface 750. A second motor 733 drives the second gear causing the first surface 750 to rotate as the shaft of the motor 733 is rotated. Thus, the first surface 750 and the second surface 760 may be rotated independently of each other.

As shown in FIG. 8, the delivery container 700 further comprises a plurality of compartments 705 of various shapes and sizes disposed within the delivery container 700 and extending from the first flat surface 750 to the second flat surface 760.

The first flat surface 750 further comprises a number of openings 751, wherein each opening 751 corresponds to a compartment 705 of the delivery container 700. Each opening 751 is large enough to allow a pushing mechanism to make contact with medications stored in each compartment 705, but is small enough to prevent medication packages stored in the compartment 705 from passing through the opening 751.

The second flat surface 760 further comprises one or more openings capable of being sequentially aligned with each compartment 705 in the delivery container 700. The second flat surface 760 may be rotated to a locked position in which no medications can pass through any opening in the second flat surface 760. To hold the second flat surface 760 in the locked position, a lock 762 may engage both the second flat surface 760 and the delivery container 700 such that the second flat surface 760 cannot be rotated or removed when the lock mechanism is set to the locked position. In one embodiment, the lock 762 may comprise a barrel lock similar to those used for bicycle locks. In another embodiment, the lock 762 may comprise a solenoid that, when actuated, prevents the second flat surface 760 from being rotated or removed from the delivery container 700. Electronics embedded in the delivery container 700 control the solenoid and securely negotiate with the electronics of the apparatus 1. The computer may communicate instructions in the form of an electronic key to the embedded electronics instructing the lock 762 to lock or unlock. The embedded electronics can also contain information relevant to the delivery container 700 and exchange information with the apparatus 1, e.g. inventory, logs, and firmware. Power is transmitted via conducting rings and brushes surrounding the delivery container 700.

The delivery container support assembly 70 may be connected to the frame 10 such that the first side of the delivery container support assembly 70 is slightly lower than the second side of the delivery container support assembly 70. When delivery container 700 engages the delivery container support assembly 70, such angling causes the delivery container to also be angled such that the first surface of the delivery container 700 is also slightly lower than the second surface of the delivery container 700. Such angling of the delivery container support assembly 70 and the delivery container 700 prevents medication packaging from falling out of the delivery container 700 if the apparatus 1 experiences vibration, shaking, or other motion.

Printer Assembly

The printer assembly prints patient information, dosage instructions, QR code barcodes for accessing additional product information, and other information on an adhesive label, and adheres the label to medication packaging to prepare the medication for being dispensed to a patient. The printer assembly comprises a printer assembly mount 810, a label printer 800, and a label handling assembly 845. The printer assembly mount 810 provides an attachment point to the frame 10 and a support surface for other printer assembly components.

As shown in FIG. 10, the label handling assembly 845 comprises a rail 850 attached to the printer assembly mount 810. A labeler carriage 870 engages and is movable along the rail 850 in a direction that is generally parallel to the rail 850 in order to move printed labels from the label printer 800 to a container disposed on the carrier 400. In one embodiment a labeler 871 comprises a flat piece of metal, plastic, or other rigid material having a first end and a second, opposite, end. The first end of the labeler 871 is attached to the labeler carriage 870. The labeler 871 is capable of being rotated around an axis positioned at the first end of the labeler 871 such that the second end of the labeler 871 can be moved between raised and lowered positions. The labeler 871 further comprises a first side and a second, opposite, side with one or more openings passing from the first side to the second side. Mounted to the first side of the labeler 871 are one or more fans 872 configured to pull air through the one or more openings in the labeler 871 such that air moves from the second side to the first side.

In order to move a printed label from the label printer 800 to a container on the carrier 400, the labeler carriage 870 is moved along the rail 850 until the labeler 871 is generally aligned with the printed label on the label printer 800. The labeler 871 is rotated around its first end such that the labeler 871 is placed in its lowered position near the printed label on the label printer 800. The one or more fans 872 are powered, causing air to pass from the second side of the labeler 871 to the first side of the labeler 871; thus causing the non-adhesive side of the label to temporarily cling to the labeler 871. Labeler 871 is then rotated about its first end to its raised position, and the labeler 871 is moved along the rail 850 until the labeler 871 and printed label are generally aligned with the container being held on the carrier 400. The labeler 871 is then rotated around its first end such that the labeler 871 is placed in its lowered position, and the adhesive side of the label engages the container on the carrier 400. The container on the carrier 400 may be rotated to wrap the label around the container; thus fully adhering the label to the container.

The label printer 800 is attached to the printer assembly mount 810, and is configured to print labels for placement on medication packaging dispensed by the apparatus 1. In one embodiment, the label printer 800 may comprise a commercially available label printer.

A dispensing chute 830 is positioned near the label handling assembly 845. Medication that has been labelled and approved for dispensing is placed into an opening of the dispensing chute 830, travels through the dispensing chute 830, and exits the dispensing chute 830 through a dispensing window 840 that is accessible from the outside of the apparatus 1. Rejected medication may be directed through a rejection chute.

A barcode scanner for reading barcodes on medication packaging may be mounted near the label handling assembly 845. In addition, an internal camera for capturing images of the medication packaging may be mounted near the label handling assembly 845. Using barcode reading software, the barcode scanner may be implemented with a camera.

Computer and Centralized Database

A computer mounts to the frame 10, and controls the function of all sub-systems of the apparatus 1. The computer may communicate electronically with a centralized database that contains patient information, medication information, drug interaction information, and other data relevant to the dispensing of medications. Data storage components installed on the computer may store information regarding the types and locations of all medications stored in the inventory storage container 20. The types and locations of all medications stored in the inventory storage container 20 may also be communicated by the computer to the centralized database.

The computer may communicate with a centralized database that stores information for all installations of the apparatus 1. The centralized database may contain drug interaction information, client information, information regarding what medications are stored in each installation of the apparatusl, and other data. The computer may communicate with the centralized database to obtain information stored in the centralized database and to upload information regarding transactions the apparatus 1 has engaged in.

Users (patients, doctors, pharmacists, etc.) may interact with the centralized database to determine where they can find an apparatus 1 that contains the medications they need. If a user needs multiple medications, then the user may be advised where the closest apparatus 1 having all of their medications is located. If there isn't apparatus 1 that has everything the user needs, then the necessary medications can be ordered and stocked in an apparatus 1 in a location that is convenient for the user. Trends can be mined from dispensing information to predict an optimal inventory for a particular apparatus 1. As the optimal inventory changes or products expire, the old stock can be discarded via the rejection chute.

Each major sub-assembly of the apparatus 1 has a separate controller in communication with the computer, and the separate controllers are networked together.

In one embodiment, the computer comprises a commercially available personal computer.

Input Device

The input device 100 mounts to the frame 10, and allows users to interact with the apparatus 1. In one embodiment, the input device 100 comprises a touchscreen monitor. In other embodiments, the input device 100 may comprise a monitor, keyboard, mouse, magnetic strip reader, RFI reader, NFC reader, or other equipment capable of allowing a user to input and receive data from the apparatus 1. One or more external cameras may be installed on the apparatus 1. Such cameras may be configured to capture images of technicians and users interacting with the apparatus 1 and communicate the image capture data to the computer and to the centralized database.

Methods

As shown in FIG. 13, a method 900 for restocking medications in the apparatus 1 begins at step 905 with providing a locked delivery container 700 filled with medications. The delivery container 700 may be provided by a pharmaceutical manufacturer, pharmacist, or other supplier of medications. In one embodiment, the provider unlocks the delivery container 700, allowing the delivery container enclosure 701 to be opened and exposing the delivery container compartments 705 to be filled. After filling the delivery container 700, the provider locks the delivery container 700, and the filled and locked delivery container 700 can then be provided to a technician for placement in an apparatus 1.

In another embodiment of the delivery container 700, unlocking the delivery container 700 allows the second flat surface 760 of the delivery container 700 to rotate. The second flat surface 760 is rotated to sequentially align the openings in the second flat surface 760 with the compartments 705 of the delivery container 700, and medications are placed in the delivery container compartments 705 as needed. After placing the medications in the delivery container 700, the second flat surface 760 is rotated to the locked position in which no opening in the second flat surface 760 aligns with any of the compartments 705 of the delivery container 700, and the lock 762 is placed in its locked position to prevent removal or rotation of the second flat surface 760 of the delivery container 700. The filled and locked delivery container 700 can then be provided to a technician for placement in an apparatus 1.

The method continues at step 910 in which the technician logs in to the apparatus 1 by entering identifying information via the input device 100. The computer transmits the entered identifying information to the centralized database to verify if the technician is authorized to access the apparatus 1. If the computer determines from the centralized database that the technician is authorized to access the apparatus 1, then the computer actuates an access panel lock to its open position at step 915 to allow the technician to open a delivery container access panel 5.

If the apparatus 1 contains an empty delivery container 700, the technician removes the empty delivery container 700 from the apparatus 1. The empty delivery container 700 may be returned to the supplier to be reused. At step 920, the technician places the filled and locked delivery container 700 in the apparatus 1. In certain embodiments, the filled and locked delivery container is placed in the apparatus 1 such that the notches disposed around the circumference of the second flat surface 760 of the delivery container 700 engage the gear of the delivery container support assembly 70 corresponding to the second flat surface 760, and the notches disposed around the circumference of the first flat surface 750 of the delivery container 700 engage the gear of the delivery container support system 70 corresponding with the first flat surface 750. The technician then closes the delivery container access panel 5, and the computer actuates the delivery container access panel lock to its closed position at step 925. The delivery container 700 replacement process is monitored by the computer. A sensor associated with the access door of the apparatus 1 and connected to the computer senses whether the access door is open or closed. If software running on the computer determines that the delivery container access panel 5 has been open longer than a predetermined amount of time allotted for a delivery container 700 replacement, an alert can be issued. In addition, an external camera may capture images of the technician performing the delivery container 700 replacement for security purposes.

Immediately after a stocked delivery container 700 is placed in the apparatus 1, the computer and centralized database may not contain any information about what medications are stored in the delivery container 700. The identity of each medication is determined during a delivery container 700 unloading process that is initiated by software running on the computer after a stocked delivery container 700 has been placed in the apparatus 1. The delivery container 700 unloading process may proceed at night or during another period of inactivity.

Maintenance of the apparatus 1 proceeds in a similar manner to method 900, but instead of replacing the delivery container 700, the technician performs the prescribed maintenance after access is granted to internal components of the apparatus 1. The maintenance process is monitored by the computer. A sensor associated with an access door of the apparatus 1 and connected to the computer senses whether the access door is open or closed. If software running on computer determines that the access door has been open longer than a predetermined amount of time allotted for the prescribed maintenance, an alert can be issued. In addition, an external or external camera may capture images of the technician performing the maintenance for security purposes.

As shown in FIG. 14, a method 880 for unloading the delivery container 700 begins at step 881. After the computer determines that the apparatus 1 is closed (i.e., not being maintained or restocked), the enclosure of the delivery container 700 is opened at step 881.

To retrieve a medication container from a delivery container compartment 705, at step 882, the computer sends instructions to the motor controllers controlling the upper carrier track motor 440, lower carrier track motor 445, and the carrier carriage motor 470 to position the carrier 400 such that the extendable member 481 is generally aligned with the delivery container compartment channel 706 that corresponds to the compartment 705 to be unloaded.

At step 883, the medication container in the delivery container compartment 705 that is closest to the carrier is pulled out of the delivery container compartment 705 and onto the carrier 400. To retrieve each medication container from the delivery container 700, the extendable member motor 486 is rotated in a first direction, causing extendable member 481 to uncoil and extend beneath the container engaging surfaces 480 and into the delivery container compartment channel 706 associated with the delivery container compartment 705. When the first flipper end 487 has reached the end of the medication container in the delivery container compartment 705 that is furthest from the carrier 400, flipper 482 is actuated to rotate about the first flipper end 487 in a first direction until flipper 482 forms an approximately 90 degree angle to extendable member 481. The extendable member motor 486 is then rotated in a second direction, causing extendable member 481 to retract, and causing flipper 482 to engage a surface of the container in the delivery container compartment 705 that is furthest from the carrier 400, pulling the container toward the carrier 400. As the medication container furthest from the carrier 400 is pulled toward the carrier 400, each additional container situated between the furthest container and the carrier 400 is also pulled toward the carrier 400. This motion of the extendable member 481 continues until a sensor indicates that a container is disposed on the container engaging surfaces 480. At this point, flipper 482 is actuated to rotate about the first flipper end 487 in a second direction until flipper 482 is generally parallel to extendable member 481 and can pass beneath the container engaging surfaces 480.

At step 886, the barcode of the medication container on the carrier 400 is scanned by a barcode reader as the medication package is rotated on the carrier 400. The barcode reader communicates the barcode to the computer. Each medication sold has a unique barcode displayed on the medication packaging. Equipped with the barcode, the computer can query the central database to determine the type of medication, quantity of medication, the dimensions of the packaging, and other information associated with the unique barcode and stored in the central database. The computer identifies a compartment 220 in the inventory storage container 20 that can accommodate the newly added medication.

At step 887, the medication container being held on the carrier 400 is placed into the inventory storage container compartment 220 chosen by the computer. The carrier 400 is moved such that the extendable member 481 is generally aligned with the channel 221 of the chosen inventory storage container compartment 220. Extendable member motor 486 is rotated as needed to position second flipper end 488 near the end of the container on the carrier 400 that is furthest from the inventory storage container compartment 220. Flipper 482 is then actuated to rotate about the first flipper end 487 in a first direction until flipper 482 forms an approximately 90 degree angle to extendable member 481. The extendable member motor 486 can then be rotated in a first direction, causing extendable member 481 to extend beneath the container engaging surfaces 480, and causing flipper 482 to engage the surface of the container on the carrier 400 that is furthest from the inventory storage container compartment 220, pushing the container toward the inventory storage container compartment 220. As the container on the carrier 400 is pushed into the inventory storage container compartment 220, any containers already disposed within the inventory storage container compartment 220 are pushed further into the inventory storage container compartment 220 to accommodate the container being pushed off the carrier 400. This motion of the extendable member 481 continues until a sensor indicates that the flipper 482 has reached the edge of the inventory storage container compartment 220, indicating that the container has been positioned entirely in the inventory storage container compartment 220. At this point, the extendable member motor 486 is rotated in a second direction, causing the extendable member 481 to retract, until flipper 482 can rotate without interfering with containers in the inventory storage container compartment 220. Flipper 482 is then actuated to rotate about the first flipper end 487 in a second direction until flipper 482 is generally parallel to extendable member 481 and can pass beneath the container engaging surfaces 480.

At step 888, the type and location within the inventory storage container 20 of the newly added medication is communicated to and stored in data storage components installed on the computer, and the type and location data may also be communicated and stored by the computer in the centralized database.

The method 880 proceeds by repeating steps 882, 883, 886, 887, and 888 until all medications have been removed from the compartment 705 in the delivery container 700 and placed in the inventory storage container 20.

Another embodiment for unloading the delivery container 700 is shown in FIG. 15. A method 950 for unloading the delivery container 700 begins at step 955. To unload a particular compartment 705 of the delivery container 700, the second flat surface 760 of the delivery container 700 is rotated such that one of the openings in the second flat surface 760 aligns with the compartment 705 to be unloaded at step 955. At step 960, the computer sends instructions to the motor controllers controlling the upper carrier track motor 440, lower carrier track motor 445, and the carrier carriage motor 470 to position the carrier 400 such that the extendable member 481 is generally aligned with the opening in the second flat surface 760 that corresponds to the compartment 705 to be unloaded. At step 970, the medication container in the delivery container compartment 705 that is closest to the carrier is pulled out of the delivery container compartment 705 and onto the carrier 400. To retrieve each medication container from the delivery container 700, the extendable member motor 486 is rotated in a first direction, causing extendable member 481 to uncoil and extend beneath the container engaging surfaces 480 and into the opening in the second flat surface 760 associated with the delivery container compartment 705. When the first flipper end 487 has reached the end of the medication container in the delivery container compartment 705 that is furthest from the carrier 400, flipper 482 is actuated to rotate about the first flipper end 487 in a first direction until flipper 482 forms an approximately 90 degree angle to extendable member 481. The extendable member motor 486 is then rotated in a second direction, causing extendable member 481 to retract, and causing flipper 482 to engage a surface of the container in the delivery container compartment 705 that is furthest from the carrier 400, pulling the container toward the carrier 400. As the medication container furthest from the carrier 400 is pulled toward the carrier 400, each additional container situated between the furthest container and the carrier 400 is also pulled toward the carrier 400. This motion of the extendable member 481 continues until a sensor indicates that a container is situated on the container engaging surfaces 480. At this point, flipper 482 is actuated to rotate about the first flipper end 487 in a second direction until flipper 482 is generally parallel to extendable member 481 and can pass beneath the container engaging surfaces 480.

At step 975, the barcode of the medication container on the carrier 400 is scanned by a barcode reader as the medication package is rotated on the carrier 400. The barcode reader communicates the barcode to the computer. Each medication sold has a unique barcode displayed on the medication packaging. Equipped with the barcode, the computer can query the central database to determine the type of medication, quantity of medication, the dimensions of the packaging, and other information associated with the unique barcode and stored in the central database. The computer identifies a compartment 220 in the inventory storage container 20 that can accommodate the newly added medication.

At step 980, the medication container being held on the carrier 400 is placed into an inventory storage container compartment 220 chosen by the computer. The carrier 400 is moved such that the extendable member 481 is generally aligned with the channel 221 of the chosen inventory storage container compartment 220. The extendable member motor 486 is rotated as needed to position second flipper end 488 near the end of the container on the carrier 400 that is furthest from the inventory storage container compartment 220. Flipper 482 is then actuated to rotate about the first flipper end 487 in a first direction until flipper 482 forms an approximately 90 degree angle to extendable member 481. The extendable member motor 486 can then be rotated in a first direction, causing extendable member 481 to extend beneath the container engaging surfaces 480, and causing flipper 482 to engage the surface of the container on the carrier 400 that is furthest from the inventory storage container compartment 220, pushing the container toward the inventory storage container compartment 220. As the container on the carrier 400 is pushed into the inventory storage container compartment 220, any containers already disposed within the inventory storage container compartment 220 are pushed further into the inventory storage container compartment 220 to accommodate the container being pushed off the carrier 400. This motion of the extendable member 481 continues until a sensor indicates that the flipper 482 has reached the edge of the inventory storage container compartment 220, indicating that the container has been positioned entirely in the inventory storage container compartment 220. At this point, the extendable member motor 486 is rotated in a second direction, causing the extendable member 481 to retract, until flipper 482 can rotate without interfering with containers in the inventory storage container compartment 220. Flipper 482 is then actuated to rotate about the first flipper end 487 in a second direction until flipper 482 is generally parallel to extendable member 481 and can pass beneath the container engaging surfaces 480.

At step 985, the type and location within the inventory storage container 20 of the newly added medication is communicated to and stored in data storage components installed on the computer, and the type and location data may also be communicated and stored by the computer in the centralized database.

The method 950 proceeds by repeating steps 960, 970, 975, 980, and 985 until all medications have been removed from the compartment 705 in the delivery container 700 and placed in the inventory storage container 20. Steps 955, 960, 970, 975, 980, and 985 are repeated until all compartments 705 of the delivery container 700 have been emptied and all medications stored in the delivery container 700 have been placed in the inventory storage container 20. Once the second flat surface 760 has been rotated 360 degrees, the openings in the second flat surface 760 have aligned sequentially with each compartment 705 in the delivery container 700, allowing the delivery container 700 to be completely unloaded with one rotation of the second flat surface 760.

In one embodiment, each inventory storage container compartment 220 contains a single type of medication. In other embodiments, each inventory storage container compartment 220 may contain multiple types of medication. For example, infrequently used medications may be stored behind more frequently used medications. Such placement avoids dedicating an entire compartment 220 to infrequently used medications while allowing frequently used medications to be accessed quickly. Resorting and optimizing of inventory can be done during otherwise idle time. Any free compartment 220 can be used to temporarily store paid for and labeled medications.

As shown in FIG. 16, a method 1000 for dispensing medications begins at step 1005 in which a user logs in to the apparatus 1 by entering identifying information via the input device 100. The computer transmits the entered identifying information to the centralized database to verify if the user is authorized to refill prescriptions using the apparatus 1.

If the computer determines from information stored in the centralized database that the user is authorized to use apparatus 1, then the computer queries the centralized database to determine if the user has a valid prescription at step 1010. If the user has a valid prescription, the centralized database communicates the original prescription to the computer, and the method proceeds to step 1015 in which the computer queries the centralized database to determine if the requested medication is stored in the inventory storage container 20. Once a user selects to use a particular apparatus 1, a hold is placed on the requested medication at the centralized database. If the requested medication is not available from the apparatus 1, the unavailability is communicated to the user via the input device 100, and the transaction may be terminated. The computer may also query the centralized database to determine what other medications the user has filled to determine of any drug interactions that may occur if the patient takes the newly prescribed medication. If a drug interaction is determined, then a message indicating the drug interaction is communicated to the pharmacist for verification.

If the requested medication is available from the apparatus 1, then the method proceeds to step 1020 in which the computer communicates instructions to the motor controllers controlling the upper carrier track motor 440, lower carrier track motor 445, and the carrier carriage motor 470 to position the carrier 400 such that the extendable member 481 is generally aligned with the storage container compartment channel 221 that corresponds to the inventory storage container compartment 220 where the requested medication is stored.

At step 1030, the medication container in the storage container compartment 220 that is closest to the carrier is pulled out of the storage container compartment 220 and onto the carrier 400. To retrieve the medication container from the storage container 20, the extendable member motor 486 is rotated in a first direction, causing extendable member 481 to uncoil and extend beneath the container engaging surfaces 480 and into the storage container compartment channel 221 corresponding to the storage container compartment 220 that contains the medication container to be retrieved. When the first flipper end 487 has reached the end of the medication container in the storage container compartment 220 that is furthest from the carrier 400, flipper 482 is actuated to rotate about the first flipper end 487 in a first direction until flipper 482 forms an approximately 90 degree angle to extendable member 481. The extendable member motor 486 is then rotated in a second direction, causing extendable member 481 to retract, and causing flipper 482 to engage a surface of the container in the storage container compartment 220 that is furthest from the carrier 400, pulling the container toward the carrier 400. As the medication container furthest from the carrier 400 is pulled toward the carrier 400, each additional container disposed between the furthest container and the carrier 400 is also pulled toward the carrier 400. This motion of the extendable member 481 continues until a sensor indicates that a container is situated on the container engaging surfaces 480. At this point, flipper 482 is actuated to rotate about the first flipper end 487 in a second direction until flipper 482 is generally parallel to extendable member 481 and can pass beneath the container engaging surfaces 480. If multiple types of medication are stored in the storage container compartment 220 where the medication container to be retrieved is stored, then the retrieved container may be placed in another storage container compartment 220, and step 1030 repeated until the desired medication container has been pulled onto the carrier 400.

At step 1035, the barcode reader reads the barcode from the retrieved medication package as the medication is rotated on the carrier 400, and the barcode reader communicates the barcode to the computer. An image of the medication package may also be captured as the medication is rotated, and the image may be communicated to the computer.

At step 1040, the computer compares the barcode read by the barcode reader to the barcode that corresponds to the requested medication. If the barcode read by the barcode reader does not match the expected barcode that corresponds to the requested medication, the medication package is discarded through a discard chute, and steps 1015, 1020, 1030, 1035, and 1040 are repeated until the correct medication is retrieved or the computer indicates that the requested medication is not present in the apparatus 1.

If the barcode read by the barcode reader matches the expected barcode for the requested medication, the method proceeds to step 1045 in which the computer communicates instructions to the label printer 800 for printing a label containing patient information such as the patient's name and dosage instructions. A QR code may also be included on the label to enable the user to obtain more information using software running on their personal cell phone or other device. The printed label extends from the label printer 800. In order to move the printed label from the label printer 800 to the container on the carrier 400, the labeler carriage 870 is moved along the rail 850 until the labeler 871 is generally aligned with the printed label on the label printer 800. The labeler 871 is rotated around its first end such that the labeler 871 is placed in its lowered position near the printed label on the label printer 800. The one or more fans 872 are powered, causing air to pass from the second side of the labeler 871 to the first side of the labeler 871; thus causing the non-adhesive side of the label to temporarily cling to the labeler 871. Labeler 871 is then rotated about its first end to its raised position, and the labeler 871 is moved along the rail until the labeler 871 and printed label are generally aligned with the container being held on the carrier 400. The labeler 871 is then rotated around its first end such that the labeler 871 is placed in its lowered position, and the adhesive side of the label engages the container on the carrier 400. The container on the carrier 400 may be rotated to wrap the label around the container; thus fully adhering the label to the container.

At step 1046, one or more images of the medication packaging may be captured by the camera as the medication packaging is rotated on the carrier 400. In one embodiment, an image of the medication packaging is captured both before and after the label is adhered to the medication packaging. The captured images may be communicated to the computer and to the centralized database.

At step 1050, the computer communicates the original prescription, the image of the unlabeled medication packaging, and the image of the labeled packaging to the centralized database. The centralized database notifies the pharmacist that there is a prescription that needs to be verified. The pharmacist views the original prescription and the images pertaining to the pending prescription, and approves or rejects dispensing of the medication based on a visual inspection of the medication. Prior to approving release of the container of medication to the user, the pharmacist may match one or more of the drug product (e.g. as determined by viewing the images of the labeled and unlabeled medication container), the National Drug Code (NDC) for the medication, the label that has been applied to the container of medication, and the prescription. If the pharmacist rejects dispensing the medication, then a message is displayed to the user via input device 100. If the pharmacist approves dispensing the medication, the user is prompted via the input device 100 to enter payment information using a magnetic strip reader or other payment input means, and the method proceeds to step 1060 in which the medication is placed in the dispensing chute 830, and the user may access the dispensed medication through the dispensing window 840. In another embodiment, the dispensed medication may be placed in a locked holding area in the apparatus 1 and made available to the user following further authentication. If a dispensed medication will not be available immediately, the input device 100 will display an estimate of how much time remains before the dispensed medication will be available, and will request a phone number for the purpose of sending a text message to the user when the dispensed medication is ready to pick up.

To facilitate use of the apparatus 1 to dispense a prescription, in one embodiment a recorded message may play on the input device 100 to encourage users to touch the touchscreen or otherwise begin interacting with the apparatus 1. The recorded message may feature an image of a welcoming character to put the user at ease with using the apparatus 1, and in one embodiment the appearance of the character may change depending on the language option that the user chooses. In another embodiment, the character that appears may be an image of the user's doctor. The message may provide step-by-step instructions to guide the user through using the apparatus 1 to dispense a medication. The use of a recorded message and welcoming image is intended to make the user comfortable with using the apparatus 1, and is advantageous because it may prevent the user from calling a pharmacist to complete the transaction.

Instructions for calling a pharmacist for a consultation may be provided via the input device 100. In one embodiment, the user may be instructed of a phone number to call via the input device 100. In another embodiment, the user may provide a phone number for a pharmacist to call for a consultation.

Data stored in the centralized database may be used to recognize trends in dispensing data, and to anticipate what types of medications may be required in a particular apparatus. For example, trend data may indicate when flu medications should be distributed to installations of the apparatus 1 in advance of flu season. To facilitate medications that are refilled regularly, the apparatus 1 may be pre-stocked to ensure that the refill medications are available when the user is likely to refill the prescription. Centralized storage of data also provides for the ability to provide data to users using remote software, for example an application running on a cell phone or similar device. The remote software may allow a user to identify the installation of the apparatus 1 nearest to their geographic location that contains all medications the user requires.

By coordinating through the centralized database, it is possible to use web-based and application based programs to locate the best apparatus 1 from a user's current location and to place a hold on a medication, provide payment, etc. For example, the application may rank apparatus 1 locations based on proximity to the user, availability of requested medications, or other user-specified criteria. To limit the space consumed by on-hold prepaid items, either through normal interaction or web interface, a technician can move the product from the apparatus 1 to a lock box. Access to the lock box is controlled by the apparatus 1.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An apparatus for retrieving one or more items stored in a vending machine comprising:
   a carriage;
   an extendable member having a first end and a second end, wherein the first end of the extendable member is connected to the carriage;
   a flipper having a first end and a second end, wherein the first end of the flipper is rotatably connected to the second end of the extendable member;
   one or more surfaces connected to the carriage;
   wherein the flipper is configured to rotate between a first position and a second position,
   wherein the flipper is generally aligned with the extendable member and the flipper and extendable member are configured to extend beneath the one or more items stored in the vending machine when the flipper is in its first position; and
   wherein the flipper is configured to engage a surface of the one or more stored items that is furthest from the carriage, and pull the one or more stored items toward the carriage when the flipper is in its second position.

2. The apparatus of claim 1 wherein the extendable member comprises a chain.

3. The apparatus of claim 1 wherein the extendable member is rigid when extended.

4. The apparatus of claim 1 wherein the flipper is configured to engage the one or more items stored in the vending machine when the flipper is in its second position.

5. The apparatus of claim 4 wherein the flipper is configured to move the one or more items onto the one or more surfaces when the extendable member is moved in a first direction, and wherein the flipper is configured to move the one or more items off of the one or more surfaces when the extendable member is moved in a second direction.

6. The apparatus of claim 5 wherein the one or more surfaces are configured to rotate, and wherein such rotation causes the one or more items item positioned on the one or more surfaces to rotate.

* * * * *